United States Patent [19]

Kim

[11] 4,137,047
[45] Jan. 30, 1979

[54] METHOD OF DETERMINING CORROSION RESISTANCE OF ANODIZED ALUMINUM

[75] Inventor: Duk H. Kim, Bellevue, Wash.

[73] Assignee: Boeing Commercial Airplane Company, Seattle, Wash.

[21] Appl. No.: 836,942

[22] Filed: Sep. 27, 1977

[51] Int. Cl.² ............... G01N 7/18; G01N 17/00; G01N 33/20
[52] U.S. Cl. .................................................. 23/230 C
[58] Field of Search .................... 23/230 C, 253 C

[56] References Cited

U.S. PATENT DOCUMENTS

| 2,827,724 | 3/1958 | Edds | 23/253 C X |
| 2,902,348 | 9/1959 | Ostrander | 23/230 C |

*Primary Examiner*—Robert M. Reese
*Attorney, Agent, or Firm*—Bernard A. Donahue; Morris A. Case

[57] ABSTRACT

Chromic acid anodized aluminum is placed in an enclosed container and covered with an aqueous alkali metal hydroxide solution. The rate of formation of hydrogen gas generated by the chemical interaction of the aluminum and the hydroxide determines corrosion resistance of the anodic film.

4 Claims, 2 Drawing Figures

METHOD OF DETERMINING CORROSION RESISTANCE OF ANODIZED ALUMINUM

BACKGROUND OF THE INVENTION

One of the better environmentally resistant coatings for aluminum is prepared by chromic acid anodizing, and therefore many structural aluminum parts are anodized with chromic acid or a dichromate. It is known to determine the corrosion resistance of a chromic ion anodized aluminum by use of a salt spray continuous exposure test that requires fourteen days. During the testing all production anodized parts have gone on to the next steps in production under an uncertainty as to quality. Should the test show a defective anodize, the production part must be removed. Therefore, it would be desireable to have a quick method of testing the anodized coat on aluminum structures. In U.S. Pat. No. 2,902,348, a drop of an acidic ferric chloride-potassium ferricyanide solution when placed onto a chromate coated aluminum would change color within a minute, provided the coating was defective.

It was discovered that a reliable quantitative test of the corrosion resistance of a chromic acid anodized coating for aluminum could be completed in about 30 minutes.

SUMMARY OF THE INVENTION

The corrosion resistance of an anodized coating on aluminum is determined by immersing the anodized aluminum in an aqueous alkali metal hydroxide solution wherein the hydroxide comprises up to about 1% by weight, and recording the time required to generate hydrogen.

It is an object of this invention to quickly determine the corrosion resistance of an anodized coating on aluminum.

It is another object of this invention to quantitatively determine the corrosion resistance of an anodized coating on aluminum.

DETAILED DESCRIPTION

When aluminum is anodized in a chromic-ion solution, the aluminum is covered with an aluminum oxide coating that will provide excellent corrosion resistance. When a completely coated surface is contacted by an aqueous alkali metal hydroxide solution the following chemical reaction takes place.

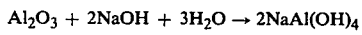
$$Al_2O_3 + 2NaOH + 3H_2O \rightarrow 2NaAl(OH)_4$$

When there is an excess of the electrolyte and once the aluminum oxide is used up to expose the bare aluminum, a different reaction takes place.

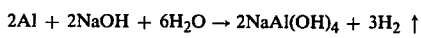
$$2Al + 2NaOH + 6H_2O \rightarrow 2NaAl(OH)_4 + 3H_2 \uparrow$$

As long as the anodic oxide protects the aluminum from the reaction with the corrosive electrolyte, there will be no release of nascent hydrogen; however, if the coating is defective, hydrogen will immediately start to evolve.

Figure 1:
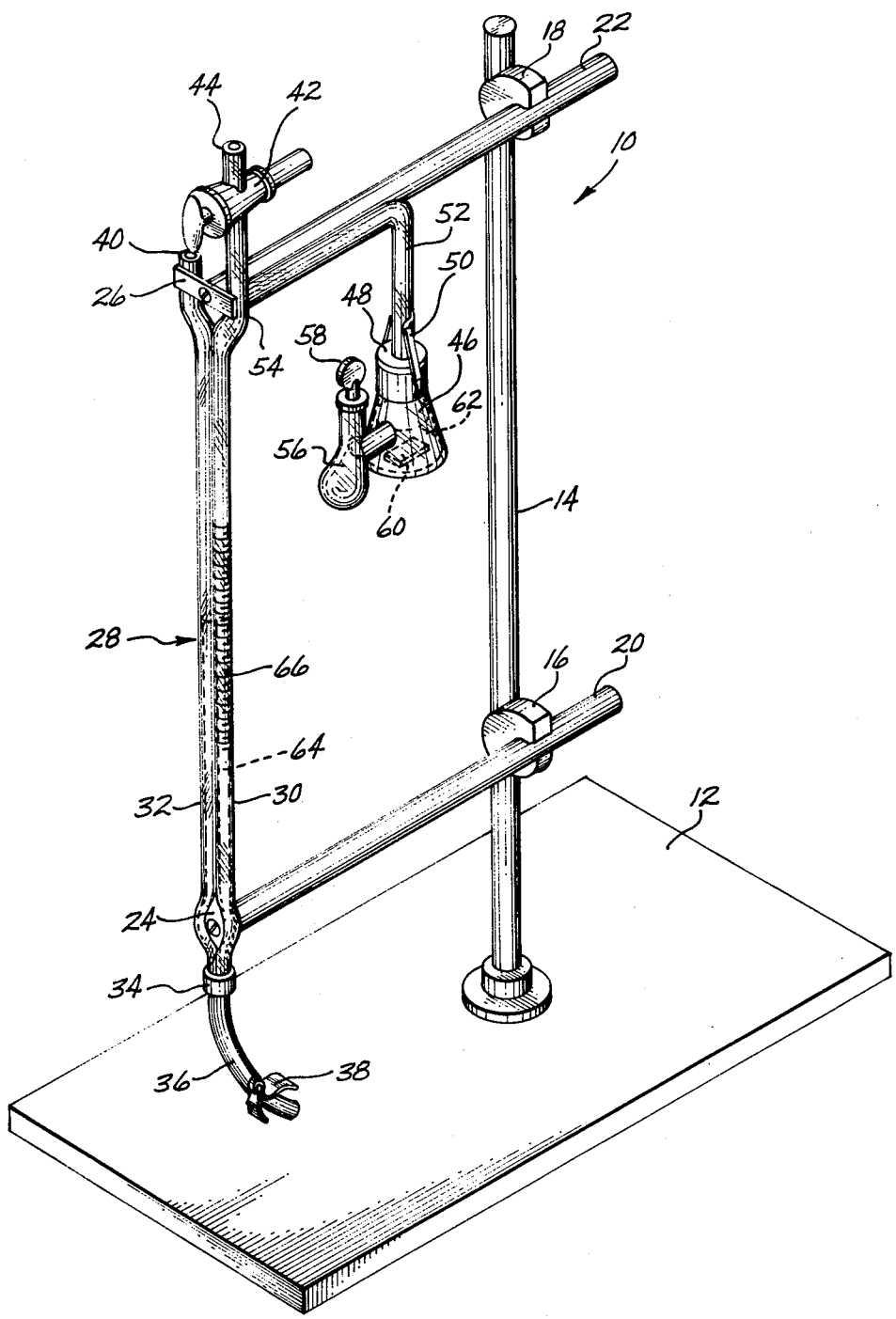
FIG. 1 shows a perspective view of apparatus used in this invention.

A preferred method of evaluating corrosion resistance utilizes equipment 10 as shown in FIG. 1. In that figure, base number 12 with connected stand 14 has clamps 16 and 18 for holding support members 20 and 22. The support members in turn have cross members 24 and 26 for attaching to a manometer 28. The manometer is a U-tube with legs 30 and 32 connected together at the ring 34 which in turn connects hose 36. The hose is closed off with clamp 38. The upper end 40 of leg 32 is open to atmosphere while pet cock 42 permits control of the opening at the end 44 of leg 30. A reactor 46 has removable stopper 48 with clamp 50 to fasten the reactor to tube 52 which directly connects into and communicates with leg 30 at juncture 54. The reactor also has connecting feeder chamber 56 which may be closed off with stopper 58.

When using this equipment for testing, structural aluminum members and a test coupon 60 are anodized under identical conditions. The coupon is placed in the reactor 46, and a solution of an aqueous alkali metal hydroxide 62 is used to cover the coupon. Any hydrogen generated within the reactor will displace the fluid 64, which is preferably water with the amount of displacement measured by the graduations 66.

Figure 2:
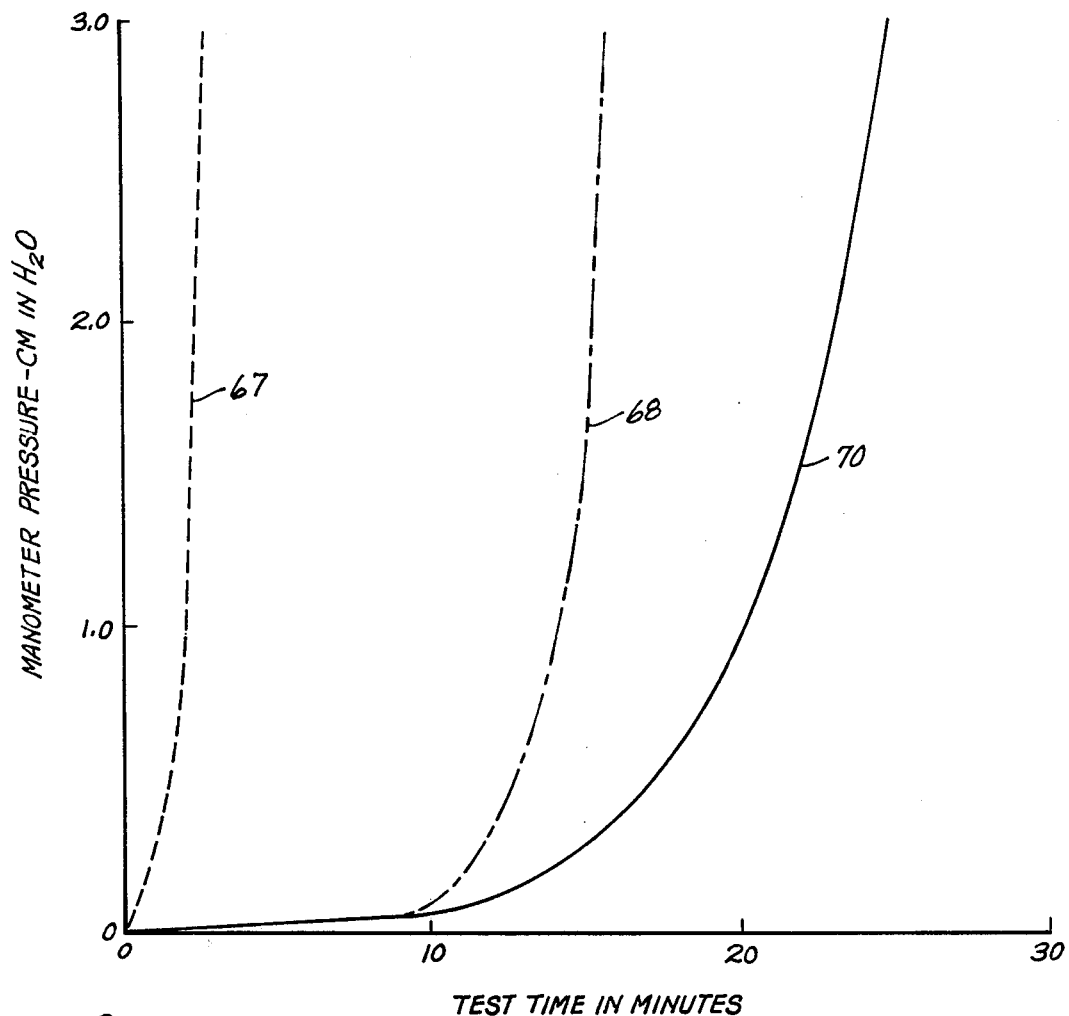
FIG. 2 shows a time versus displacement graph depicting this invention.

It was found that when using an hydroxide concentration of up to about 1% by weight that the test is effective and permits quantitative evaluation of the corrosion resistance of the anodized coating on the aluminum, with about a 0.1% by weight concentration preferred and the time determined for displacing 3cm of water in the manometer. Numerous tests using the 0.1% concentration were performed with the aluminum in three different conditions; (1) untreated aluminum, (2) aluminum anodized with a chromic-ion anodizing solution, and (3) aluminum anodized as in 2 then sealed for about 20 minutes in a deionized water bath at 160° F. FIG. 2 shows a chart of time versus displacement having three distinct lines each of which were obtained by summing all the tests for the three conditions of the aluminum. Line 67 represents the sum of all the tests of the untreated aluminum, line 68 the sum of the tests on anodized aluminum and line 70 the sum of tests on anodized aluminum further sealed in deionized water. It is readily apparent from this chart that the process gives quantitative results. Tests were performed using sodium hydroxide and also using potassium hydroxide as the results were comparable.

I claim:

1. A method of evaluating corrosion resistance of a coating generated on aluminum by chromic acid anodizing, the method comprising: covering anodic coating aluminum with an aqueous alkali metal hydroxide having a concentration of up to about 1% by weight of hydroxide, directing hydrogen generated by a reaction between aluminum and the hydroxide into a displacement indicating means, and determining corrosion resistance of the coating by measuring time versus displacement.

2. A method of evaluating corrosion resistance of a coating on aluminum as in claim 1 further comprising selecting a concentration of the aqueous alkali metal hydroxide of about 0.1% by weight of the hydroxide.

3. A method of evaluating corrosion resistance of a coating generated on aluminum by chromic-ion anodizing, the method comprising: anodizing a test coupon and a part under identical conditions, placing the test coupon in a reactor, providing for communication between the reactor and a manometer, covering the test coupon inside the reactor with an aqueous alkali metal hydroxide having a concentration up to about 1% by weight of the hydroxide, and determining corrosion resistance of the anodic coating on the test coupon by measuring time versus displacement within the manometer by hydrogen generated in the reactor by interaction between the aluminum and the hydroxide.

4. A method of evaluating corrosion resistance of a coating generated on aluminum as in claim 3, steps further comprising: selecting an aqueous alkali metal hydroxide having a concentration of about 0.1% hydroxide by weight, and determining the time for displacing 3cm of water in the manometer.

* * * * *